US007722891B2

(12) United States Patent
Barthel et al.

(10) Patent No.: US 7,722,891 B2
(45) Date of Patent: May 25, 2010

(54) MULTIPLE EMULSIONS

(75) Inventors: Herbert Barthel, Emmerting (DE); Bernard Paul Binks, Walkington (GB); Amro Dyab, Hull (GB); Paul Fletcher, Hull (GB)

(73) Assignee: Wacker Chemie AG, Munich (DE)

( * ) Notice: Subject to any disclaimer, the term of this patent is extended or adjusted under 35 U.S.C. 154(b) by 656 days.

(21) Appl. No.: 10/376,811

(22) Filed: Feb. 28, 2003

(65) Prior Publication Data

US 2003/0175317 A1 Sep. 18, 2003

(30) Foreign Application Priority Data

Mar. 14, 2002 (DE) ................................ 102 11 313

(51) Int. Cl.
*A61K 9/113* (2006.01)
*A61K 8/06* (2006.01)
*A61K 47/02* (2006.01)

(52) U.S. Cl. ........................ 424/400; 424/401; 514/770

(58) Field of Classification Search ................. 424/401, 424/688, 937–38, 400; 514/937–38, 770
See application file for complete search history.

(56) References Cited

U.S. PATENT DOCUMENTS

| | | | | |
|---|---|---|---|---|
| 5,833,967 | A * | 11/1998 | Ramin | 424/70.4 |
| 6,106,847 | A | 8/2000 | Ferrero et al. | |
| 6,193,412 | B1 | 2/2001 | Osaheni et al. | |
| 6,548,050 | B1 * | 4/2003 | Bara | 424/64 |
| 2002/0077372 | A1 | 6/2002 | Gers-Barlag et al. | |
| 2007/0111917 | A1 * | 5/2007 | Lang et al. | 510/417 |
| 2007/0209552 | A1 * | 9/2007 | Gottschalk-Gaudig | 106/287.1 |
| 2007/0281878 | A1 * | 12/2007 | Gottschalk-Gaudig et al. | 510/417 |

FOREIGN PATENT DOCUMENTS

| | | | |
|---|---|---|---|
| DE | 1163 784 | | 2/1964 |
| DE | 19 16 360 | | 10/1970 |
| DE | 23 44 388 | | 3/1975 |
| DE | 41 36 699 | | 10/1992 |
| DE | 41 27 665 | | 2/1993 |
| DE | 33 39 056 | | 5/1993 |
| DE | 43 41 113 | | 6/1995 |
| DE | 691 14 674 | | 4/1996 |
| DE | 196 38 729 | | 3/1998 |
| EP | 0 529 396 | A1 | 3/1993 |
| EP | 0 579 049 | | 1/1994 |
| EP | 0 686 676 | | 12/1995 |
| EP | 0 780 112 | A1 | 6/1997 |
| EP | 0 782 846 | A2 | 7/1997 |
| EP | 0 836 847 | A2 | 4/1998 |
| EP | 0 892 035 | | 1/1999 |
| EP | 0 926 210 | | 6/1999 |
| GB | 1152607 | | 5/1969 |
| JP | 2001-354520 | | 12/2001 |
| WO | WO 99/07463 | | 2/1999 |
| WO | WO 00/37045 | | 6/2000 |

OTHER PUBLICATIONS

Aveyard, R. et al., "Emulsions stabilised solely by colloidal particles," Advances in Colloid and Interface Science, vols. 100-102, pp. 503-546 (Feb. 2003).*

Binks, B.P., "Particles as surfactants—similarities and differences," Current Opinion in Colloid & Interface Science, vol. 7, pp. 21-41, published online on Mar. 4, 2002 in ScienceDirect.*

Binks, B.P. et al., "Influence of particle wettability on the type and stability of surfactant-free emulsions," Langmuir, vol. 16, pp. 8622-8631 (2000).*

Derwent Abstract, accession No. 2002-298197; abstracting JP 2001354520 (Dec. 2001).*

English Derwent Abstract AN:1991-369051[50] corresp. to DE 691 14 674 T2.

English Derwent Abstract AN:1995-216264[29] corresp. to DE 43 41 113 A1.

English Derwent Abstract AN:1993-067903[09] corresp. to DE 4 127 665 A1.

English Derwent Abstract AN:1998-194418[18] corresp. to DE 196 38 729 A1.

English Derwent Abstract AN:1992-358400[44] corresp. to DE 41 366 99 A.

English Derwent Abstract AN:1985-116918[20] corresp. to DE 33 39 056 A.

English Derwent Abstract AN:1975-17818W[18] corresp. to DE 23 44 388 A.

(Continued)

*Primary Examiner*—John Pak
(74) *Attorney, Agent, or Firm*—Brooks Kushman P.C.

(57) ABSTRACT

Storage stable multiple emulsions of a polar phase A1, a nonpolar phase B and a polar phase A2, or of a nonpolar phase B1, a polar phase A and a nonpolar phase B2, employ particulate solids smaller than 1 μm to stabilize the resulting A1/B/A2 or B1/A/B2 multiple emulsions against coalescence, with the proviso that surface-active substances are present only up to a maximum concentration of less than 0.1 times the critical micelle concentration of the surface-active substances in phase A, A1, A2. The multiple emulsions have numerous uses including controlled release of active substances from a dispersed phase.

14 Claims, 7 Drawing Sheets

OTHER PUBLICATIONS

English Derwent Abstract AN:1964-80970 corresp. to DE 1 163 784.

English Derwent Abstract AN:1970-71764R corresp. to DE 19 163 60 A.

English Derwent Abstract AN:1994-008697[02] corresp. to EP 0 579 049 A1.

English Derwent Abstract AN:1996-021221[03] corresp. to EP 0 686 676 A1.

English Derwent Abstract AN:1999-460396[39] corresp. to EP 0 926 210 A1.

J. Chem. Soc., 1907, 91, 2001.

Von Matsumoto et al., J. Coll. Interf. Sci., 1976, 57, 353.

English Derwent Abstract AN 1999-167247[14] Corresponding To WO 99/07463.

English Derwent Abstract AN 1993-067903[09] Corresponding To EP 0 529 396.

* cited by examiner

MULTIPLE EMULSIONS

BACKGROUND OF THE INVENTION

1. Field of the Invention

The invention relates to multiple emulsions, to their production, and to their use.

2. Background Art

Emulsions require the immiscibility of two phases. Emulsions can therefore be formed if two phases, phase A and phase B, are not completely miscible with one another. Typically, phase A is an aqueous phase, and phase B is an oily phase. Accordingly, it is possible to produce water-in-oil (w/o) and oil-in-water (o/w) emulsions.

Conventional emulsions consist of a water phase and an oil phase and one or more surface-active substances. Typically, surface-active substances are low molecular weight substances which contain one or more polar groups and also contain one or more nonpolar groups. Emulsions which are stabilized by means of particles were described for the first time by Pickering: J. CHEM. Soc., 1907, 91, 2001.

For some applications, multiphasic emulsions ("multiple emulsions") are desirable. The first experiments for the preparation of multiple emulsions were described by Matsumoto et al., J. COLL. INTERF. SCI., 1976, 57, 353. A problem with multiple emulsions is their instability toward coalescence.

Multiple emulsions using polymeric surfactants have been described in DE 41 36699 A1 and DE 33 39 056 C2. The processes disclosed, however, are complex, costly, perturbation-sensitive, and lead to high-viscosity systems. Multiple emulsions using gelling agents in the internal phase have been described in DE 196 38 729 A1. The process disclosed is based on imparting thixotropy to and thickening of the internal aqueous phase, which significantly restricts its applicability.

Multiple emulsions consist of (1) a phase X, which is present as an emulsion in a (2) phase Y, this phase X-in-phase Y emulsion (X/Y) being present (3) in turn as droplets in a further phase Z as an emulsion:

Phase X-in-phase Y-in-phase Z (Phase X/Phase Y/Phase Z).

In practice, two principal possibilities for multiple emulsions arise from this:

Possibility I: (A/B/A').

Multiple emulsions consisting of (1) a phase A which is present in emulsified form in a (2) phase B, this phase A-in-phase B emulsion (A/B) is present (3) in turn as droplets in a further phase A': phase A-in-phase B-in-phase A' (A/B/A').

Possibility II: (B/A/B').

Multiple emulsions consisting of (1) a phase B which is present in emulsified form in a (2) phase A, this phase B-in-phase A emulsion (B/A) is present (3) in turn as droplets in a further phase B': phase B-in-phase A-in-phase B' (B/A/B').

In practice, with phase A as the aqueous phase and phase B as the oily phase, it is possible to prepare multiple emulsions in the form of (I) water-in-oil-in-water emulsion (w/o/w)

or in the form of (II) oil-in-water-in-oil emulsion (o/w/o).

The stabilization of multiple emulsions known hitherto requires the use of low molecular weight oligomeric or polymeric emulsifiers or surface-active substances which stabilize the various w/o and o/w interfaces. However, multiple emulsions known hitherto suffer from coalescence and sedimentation, lack shear stability, and possess inadequate storage stability, leading to loss of their properties, lending them unsuitable for their intended applications.

It has hitherto been impossible to prepare multiple emulsions having long-term stability with feasible expenditure. For example, to date, no simple and universal process has been described which facilitates the preparation of multiple emulsions with long-term storage stability and shear stability.

Multiple emulsions are of great technical interest. They are, for example, of key technical importance in applications which require a "controlled release" function. Controlled release means the controlled and slow release of (I) active ingredients dissolved in polar aqueous phase or (II) active ingredients dissolved in nonpolar oily phase, and is of great interest in a wide variety of applications in pharmacy, medicine, agrochemistry, foodstuffs and animal feeds, in cosmetics, and in chemical catalysis.

SUMMARY OF THE INVENTION

It is an object of the invention to improve upon the prior art and, in particular, to prepare multiple emulsions which exhibit long-term stability and shear stability. A further object of the invention is to provide a simple process which can be used universally to prepare multiple emulsions. These and other objects are achieved by providing multiple emulsions comprising a polar phase A1, a nonpolar phase B and a polar phase A2 or a nonpolar phase B1, a polar phase A and a nonpolar phase B2, each multiple emulsion containing particulate solids which are smaller than 1 μm, with the proviso that surface-active substances are present only up to a maximum concentration of less than 0.1 times the critical micelle concentration of the surface-active substances in phase A, A1, or A2.

DETAILED DESCRIPTION OF THE PREFERRED EMBODIMENT(S)

Figure 1A:
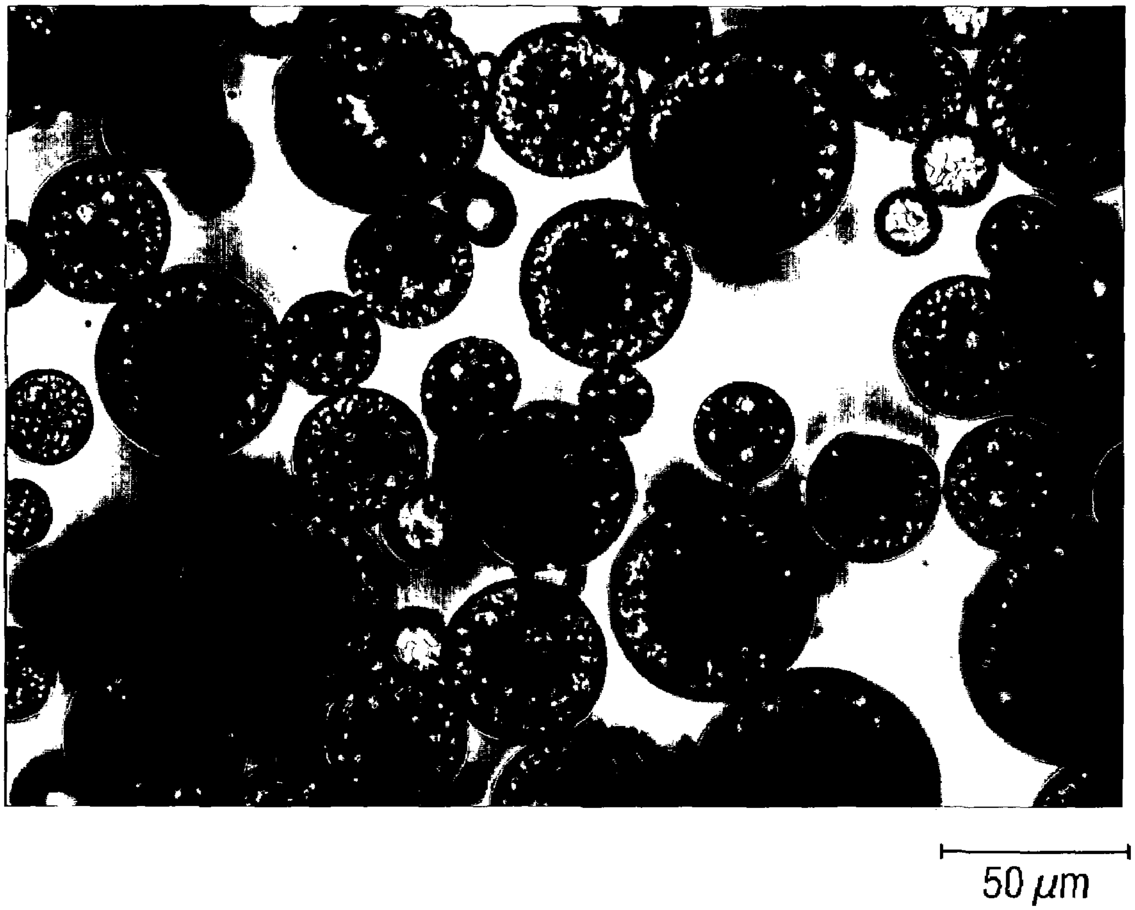
FIG. 1*a* is a photomicrograph of a water/oil/water multiple emulsion of the present invention.

Multiple emulsions, as described earlier, are conceptually possible in the form of several variants:

Variant 1:

A1-in-B-in-A2, (A1/B/A2), wherein a phase A1 is dispersed in a second phase B, which in turn is dispersed in a third phase A2. Phases A1 and A2 may be identical or different, and are chosen from the class of phase A substances as described hereafter. Phase A1 can consist of phase A2 and comprise further soluble substances. Preferably, phase A1 and phase A2 consist of the same phase A substances, and comprise one or more further identical or different soluble substances.

Variant 2:

B1-in-A-in-B2, (B1/A/B2) wherein a phase B1 is dispersed in a second phase A, which in turn is dispersed in a third phase B2. Phases B1 and B2 may be identical or different, and are chosen from the class of phase B substances as described hereafter. Phase B1 can consist of phase B2 and comprise further soluble substances. Preferably, phase B1 and phase B2 consist of the same phase B substances, and comprise one or more further identical or different soluble substances.

The A and B phases are preferably liquids. Liquids are those substances or mixtures of substances which are present in liquid or flowable form or a form which can be rendered flowable by shearing at application temperatures and pressures of the emulsions. Preference is given to working at atmospheric pressure. Preferably, the temperatures are greater than 0° C. and less than 100° C., more preferably greater than 5° C. and less than 70° C., and most preferably greater than 20° C. and less than 40° C.

The A and B phases are not completely miscible with one another. "Not completely miscible" means that the phase A can form an emulsion with phase B using suitable conventional surface-active substances (emulsifiers) in suitable amounts. For example, this generally corresponds to A being soluble in B, and vice versa, in an amount of less than 50% by weight, preferably less than 10% by weight, more preferably less than 1% by weight.

Phase A substances include water or an aqueous solution, or a non-aqueous high-polarity phase, for example consisting of amides such as formamide or dimethylformamide; glycols such as ethylene glycols; polyalcohols such as glycerol; lower alcohols such as methanol; alkylated sulfoxides such as dimethyl sulfoxide; acetonitrile; or solutions based thereon. Preferably, phase A is an aqueous system, which may include other polar liquids as just described.

Phase B substances, which can also be referred to as the oil phase, can consist of any nonpolar substances which are not completely soluble in water or in phase A when phase A is non-aqueous. Suitable phase B substances include hydrocarbons such as aromatics, for example benzene, toluene and xylene, aliphatics, for example alkanes such as pentanes, hexanes, e.g., n-hexane and cyclohexane, heptanes, octanes, e.g., n-octane and isooctanes, nonanes, decanes, undecanes, and dodecanes, alkenes, esters, ethers, polyethers, ketones, long-chain alcohols, e.g. n-octanol, organosilicon compounds such as silicones, e.g. linear or cyclic polydialkylsiloxanes, polydimethylsiloxanes having 0-10% by weight of methylsiloxy and/or trimethylsiloxy units in addition to 90-100% by weight of dimethylsiloxy units, or any mixtures thereof. These lists of phase A and phase B substances are exemplary, and not limiting.

All particulate solids are useful, in particular finely divided particulate solids which are completely soluble neither in phase A nor in phase B, and are thus present in the finished multiple emulsion as particles. Suitable particulate solids include phyllosilicates, e.g. clays, such as laponites, bentonites, and montmorillonites; solid polymers, e.g. polystyrene; inorganic carbonates such as calcium carbonates, including natural calcium carbonates, preferably ground and classified, and precipitated synthetic calcium carbonates; sulfates such as barium sulfate, e.g. natural, ground and classified barium sulfates or else precipitated barium sulfate; nitrides, e.g. boron nitride and silicon nitride; carbides, e.g. boron carbide and silicon carbide; and metal oxides, e.g. titanium dioxides, aluminum dioxides, zirconium dioxides and silicon dioxides. Among the silicon dioxides are included e.g. kieselguhr or diatomaceous earths which are natural and ground or classified by processes such as dispersion and sedimentation, and also synthetic silicon dioxides, e.g. silicon dioxides precipitated by wet-chemical methods or prepared pyrogenically in a flame. Preference is given to pyrogenic silicon dioxides which are prepared in a flame process by reacting silicon compounds which can be evaporated up to 300° C., preferably up to 150° C., e.g. $SiCl_4$, $CH_3SiCl_3$, $HSiCl_3$, $HCH_3SiCl_2$, mixtures thereof, including mixtures contaminated with other Si compounds and/or hydrocarbons up to 20% by weight, preferably up to 10% by weight, preferably in a hydrogen/oxygen flame, the latter preferably in a substantially stoichiometric mixture, "substantially" referring to less than a 20% deviation from stoichiometry.

It is possible to use any desired mixtures of the abovementioned particles. Preference is given to mixtures of hydrophilic, water-wettable and hydrophobic, water-unwettable particles. Preference is given to a mixing ratio of hydrophilic to hydrophobic particles of from 1:4 to 4:1, more preferably from 1:2 to 2:1.

Preferably, the multiple emulsions according to the invention include particulate solids which comprise at least one metal oxide, more preferably particulate solids which comprise silicon dioxide, most preferably particulate solids which comprise hydrophobic silicon dioxide or at least partially silylated silicon dioxide. In addition, preference is given to particulate solids which comprise mixtures of hydrophilic and hydrophobic silicon dioxide, and further preference is given to particulate solids which comprise pyrogenically prepared silicon dioxide.

The particle size is less than 1 micrometer, more preferably less than 100 nm and most preferably less than 30 nm, based on the average diameter of the primary particles. The specific surface area of the particles is preferably greater than 1 $m^2/g$, more preferably greater than 10 $m^2/g$, yet more preferably greater than 50 $m^2/g$, and most preferably greater than 150 $m^2/g$. The specific surface area may be determined by the BET method in accordance with DIN 66131/66132, or by other suitable methods such as CTAB absorption in accordance with ASTM D3765-85 or by image analysis of images obtained by means of transmission electron microscopy, enumerating the diameters of the primary particles, and subsequently calculating the volume distribution of the particle size and the specific surface area resulting therefrom.

For the particles according to the invention, all particle shapes are possible, such as spherical, discoid, rod-like, branched, e.g. fractal, with fractal dimensions for the mass $D_m$ of $1<D_m<3$; in a preferred embodiment, the particles are spherical; in another particularly preferred embodiment, the particles have a branched and/or fractal structure.

For the particles according to the invention, all typical material densities are possible, i.e. preferably 0.5 to 5 kg/l for primary particles, preferably 0.05 to 1 kg/l for branched, optionally fractal aggregates consisting of primary particles, and preferably 0.01 to 0.5 kg/l for branched, optionally fractal agglomerates consisting of aggregates. In this respect, the definition of primary particles, aggregates and agglomerates is in accordance with DIN 53206.

Particular preference is given to using pyrogenic silicon dioxide. The silicon dioxide preferably has an average primary particle size less than 100 nm, more preferably with an average primary particle size of from 5 to 50 nm. These primary particles generally do not exist in isolated form within the silicon dioxide, but are constituents of larger aggregates and agglomerates. The silicon dioxide preferably has a specific surface area of from 25 to 500 $m^2/g$ (measured according to the BET method in accordance with DIN 66131 and 66132).

The silicon dioxide preferably has aggregates (definition in accordance with DIN 53206) in the range of diameters from 50 to 1000 nm, and agglomerates (definition in accordance with DIN 53206) constructed from aggregates, which have sizes from 1 to 500 μm depending on the external shear stress (e.g. measurement conditions).

The silicon dioxide preferably has a surface fractal dimension of less than or equal to 2.3, more preferably less than or equal to 2.1, and most preferably of from 1.95 to 2.05, where the fractal dimension of the surface $D_s$ is defined as: particle surface A is proportional to the particle radius R to the power of $D_s$. The silicon dioxide preferably has a mass fractal dimension $D_m$ of less than or equal to 2.8, more preferably greater than or equal to 2.7, and most preferably from 2.4 to 2.6. The mass fractal dimension $D_m$ is defined as: particle mass M is proportional to the particle radius R to the power of $D_m$.

The silicon dioxide preferably has a density of surface silanol groups SiOH of less than 2.5 $SiOH/nm^2$, more preferably less than 2.1 $SiOH/nm^2$, yet more preferably of less than 2 $SiOH/nm^2$, and most preferably from 1.7 to 1.9 $SiOH/nm^2$.

It is possible to use silicon dioxides prepared at elevated temperature (>1000° C.). Particular preference is given to silicon dioxides prepared pyrogenically. It is also possible to use hydrophilic silicon dioxides which come freshly prepared direct from the burner, which have been stored temporarily, or have already been packaged in a standard commercial manner. It is also possible to use hydrophobicized silicon dioxides, e.g. standard commercial products. It is possible to use uncompacted silicon dioxides with bulk densities of less than 60 g/l, and also compacted silicon dioxides with bulk densities greater than 60 g/l. It is possible to use mixtures of different silicon dioxides, for example mixtures of silicon dioxides of varying BET surface area, or mixtures of silicon dioxides with a different degree of hydrophobicization or silylation.

The hydrophobicization, and in particular the silylation, of particles, in particular of metal oxides, and especially of silicon dioxide, can be carried out by conventional techniques known to the skilled artisan, for example as disclosed in accordance with DE 2344388, DE 1163784, DE 1916360, EP 579 049, EP 686676, EP 926210, DE ref. no. 10150274, or by comparable processes. Analysis of the coverage of particles, in particular metal oxides, and especially silicon dioxide, with hydrophobicizing agents or silylating agents, can be carried out via the determination of the carbon content from elemental analysis, via IR methods such as DRIFT and ATIR, via adsorption methods which are based on the BET methodology, as described in S. Brunnauer, P. H. Emmett and E. Teller, J. Am. Chem. Soc. (JACS), 1938, Volume 60, page 309, or in S. J. Gregg and K. S. W. Sing, "Adsorption, Surface Area and Porosity", 2nd Edition, Academic Press, New York, 1982, pages 41 ff, or in H. Barthel in "Chemically Modified Surfaces", Proceedings of the Fourth Symposium on Chemically Modified Surfaces, Philadelphia, 1991, H. A. Mottola and J. R. Steinmetz, eds., Elsevier, N.Y., 1992, page 243 and the documents cited therein, in particular documents 4-6 which describe these effects in more detail, or in Osaheni et al., U.S. Pat. No. 6,193,412. Other possible methods are inverse gas chromatography, as described in H. Balard, E. Papirer, A. Khalfi, H. Barthel, J. Weis, "From Molecules to Materials", Organosilicon Chemistry IV, N. Auner and J. Weis, eds., Wiley, Weinheim, pages 773 ff, 2000, or static volumetric gas adsorption, as described in H. Barthel, L. Roesch and J. Weis, SURFACE REVIEW AND LETTERS, Volume 4, No. 5 (1997), pages 873 ff. The determination of the acidic OH groups on metal oxide surfaces, especially the residual silicon dioxide silanol groups on the surface of silicon dioxides, can, for example, take place by acid-base titrations following the process in accordance with G. W. Sears, Anal. Chem., 28 (12) (1956) 510.

Preferably, the particles are characterized in that they are not completely wetted by phase A, i.e. have a contact angle θ in air against phase A greater than 0°; and secondly and at the same time, do not have complete unwettability toward phase A, A1 or A2 either, i.e. have a contact angle θ in air against phase A, A1 or A2 of less than 180°. The contact angle θ of the particles against phase A, A1 or A2 is preferably between 60° and 120°. Preferably, the contact angle θ of the particles against water is between 60° and 120°. The particles are finely divided solids which are preferably not completely water-wettable, i.e. those which have a surface energy γ of less than 72.5 $mJ/m^2$ and have a contact angle in air against water greater than 0°. In addition, the particles are preferably characterized in that they are completely wetted by phase B, i.e. have a contact angle θ in air of 0° against phase B.

Contact angles on powders may be measured by standard methods known to the skilled artisan:

1) The contact angle of the particles can be obtained by carefully preparing, using customary methods, a compact of the pulverulent solid consisting of particles, and subsequently determining the contact angle against a known liquid, preferably a pure substance with known surface tension in air, using conventional methods, e.g. goniometer or by digital image analysis.

The contact angle θ defines the ratio of the surface tensions and energies γ of liquids (l) and solids (s) in a gas space (g) as follows: cos(θ)=(γ(sl)−γ(sg))/γ(lg). The surface energy ($mJ/m^2$) of a solid has the same dimensions as the surface tension of a liquid (mN/m), since [J]=[N*m].

2) The contact angle can be ascertained by imbibition methods using the Lucas-Washburn equation. This is based on the imbibition of a known and defined liquid, preferably a pure substance with known surface tension, into a defined cluster, or a gently compressed compact with an open porosity and pore radius R, preferably porosity greater than 0.25, of the particle compact. The rate of imbibition dh/dt, or the height of the imbibed liquid column h, calculated from the mass increase m in liquid by the particle cluster against time t, and the viscosity of the imbibed liquid η and the surface tension γ of the imbibed liquid can be used to determine the value of the cosine of θ(cos(θ)), and thus the contact angle θ of the liquid against the particle surface for a known particle radius r by means of the equation according to Lucas-Washburn (Washburn, E. W., Phys. Rev. 17, 273 (1921) and R. Lucas Kolloid Z. 23, 15 (1918)):

$$dh/dt = r*\gamma*\cos(\theta)/(4*\eta)$$

or $$h^2 = r*\gamma*t*\cos(\theta)/(2*\eta)$$

Figure 5A:
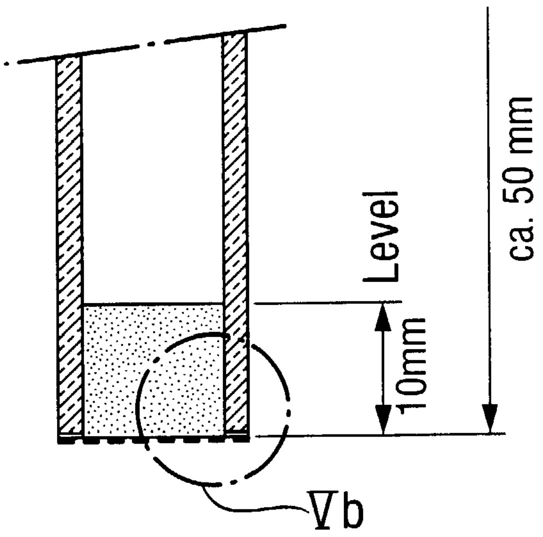
FIG. 5 illustrates a conventional technique for determining the contact angle of particulate solids with a liquid.
Figure 5B:
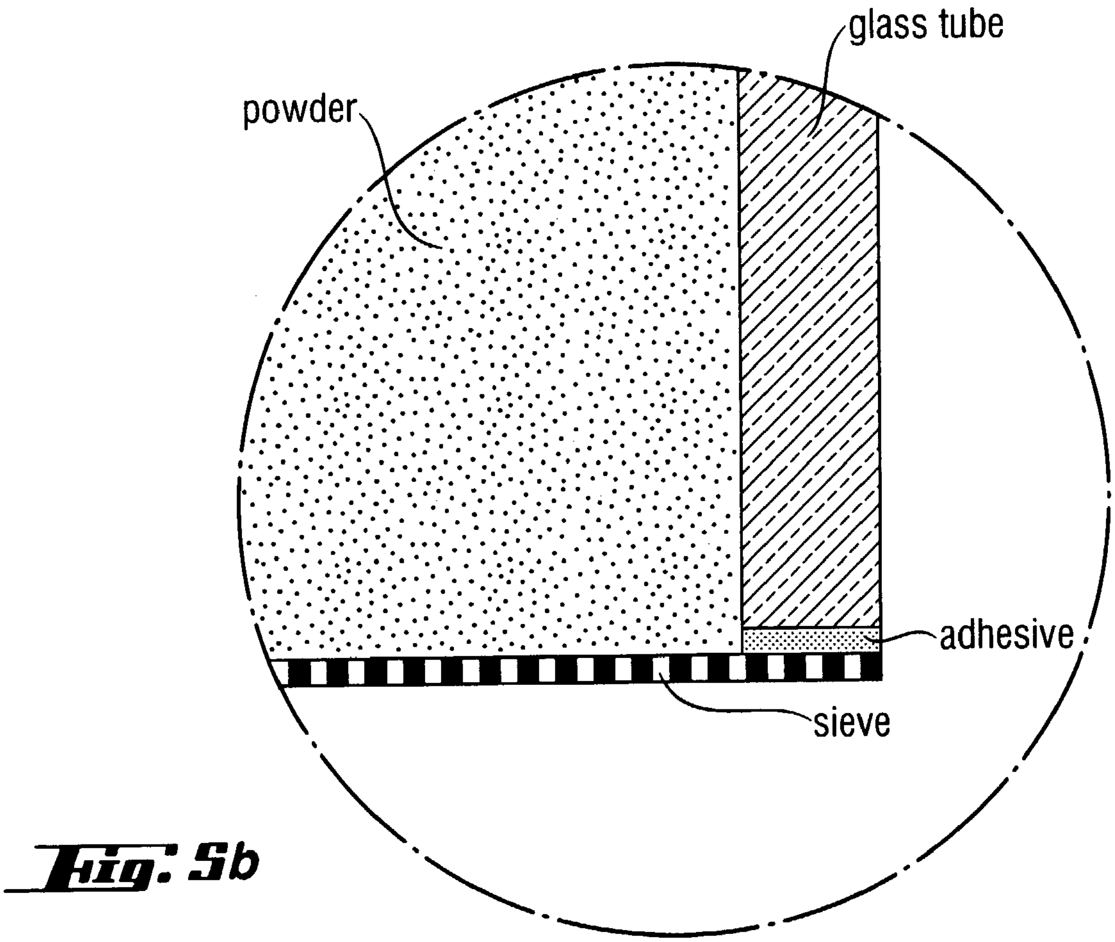

Further details relating to the description of the method are given in J. Schoelkopf et al., J. Colloid. Interf. Sci. 227, 119-131 (2000):

$$t=A\cdot m^2 \quad \text{Washburn equation}$$

where t is time and m is the mass of the imbibed liquid, and $$A=\frac{\eta}{\{C\cdot\rho^2\cdot\gamma\cdot\cos\theta\}},$$

where

η is the viscosity of the liquid, ρ is the density of the liquid, γ is the surface tension of the liquid, θ is the contact angle, liquid-powder, and C is a numerical factor, dependent on the geometric properties of the powder and sample tube. An illustration of the process is shown in FIG. 5.

Examples of measurement methods for determining the surface energy of particles include:

3) Repetition of the experiment under 1) or 2) with various liquids having different surface tensions.

3a) plot of the cosine of the contact angle θ ascertained in a Zisman plot against the surface tension γ of the liquids used, cos(θ)=f(γ) gives, as the intersection with the abscissa, the critical surface energy $\gamma_{crit}$ as a measure of the surface energy γ of the particles.

Figure 6:
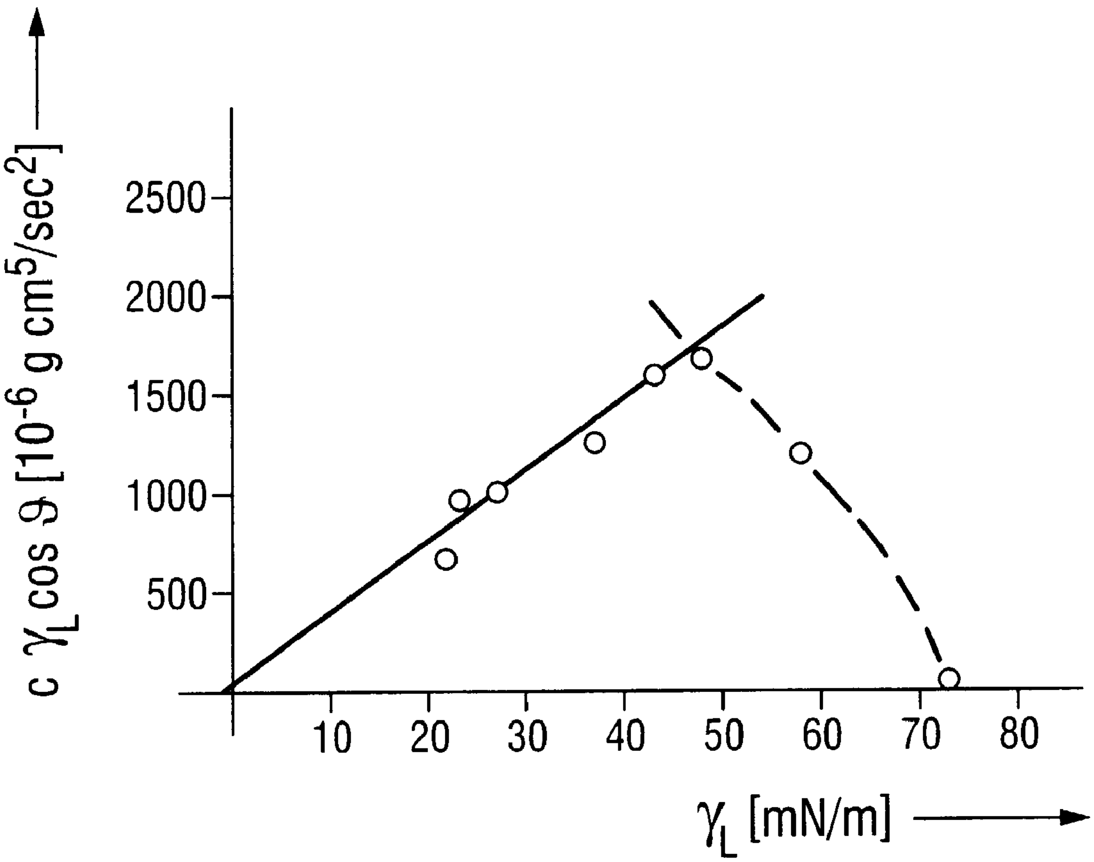
FIG. 6 is a Zisman plot of imbibition parameter A against liquid surface tension which may be used to measure critical surface energy of particles.

3b) plot of the imbibition parameter A in a Zisman plot against the surface tension γ of the liquids used produces, at the peak of the curve (maximum) as the associated abscissa value, the critical surface energy $\gamma_{crit}$ as a measure of the surface energy γ of the particles (see FIG. 6).

4) For particles which form agglomerates with bulk densities $d_{BD}$<<1 g/ml, but consisting of primary particles with material densities $d_{MD}$>1 g/ml, shaking into liquids of varying surface tension can be used as a method: in the event of nonwetting, the particle agglomerates float; in the event of wetting, the air in the agglomerates is displaced, and the particle agglomerates sink.

If various liquids with different surface tension are used, it is possible to determine exactly the surface tension of the liquid at which the particle agglomerates sink; this gives the critical surface energy $\gamma_{crit}$ as a measure of the surface energy γ of the particles.

The method can also be simplified by reducing the surface tension of water (72.5 mN/m) by adding methanol, ethanol or isopropanol:

4a) Typically, water is initially introduced, an amount of particle agglomerates is placed onto the surface of the water (floating) and then the alcohol is titrated in, with stirring. The water:alcohol ratio when the particle agglomerates sink is noted, and the surface tension is determined precisely for this water/alcohol ratio in a separate experiment using standard methods (ring detachment method, Wilhelmy method).

4b) In another embodiment, defined mixtures of water with the abovementioned lower alcohols can also be prepared, and then the surface tensions of these mixtures are determined. In a separate experiment, these water:alcohol mixtures are coated over with defined amounts of particle agglomerates (for example in the volume ratio 1:1) and shaken under defined conditions (for example gentle shaking by hand or using a tumble mixer for about one minute). The parameters determined are the water:alcohol mixture in which the particle agglomerates just do not sink and the water:alcohol mixture with a higher alcohol content in which the particle agglomerates just do sink. The surface tension of the latter alcohol:water mixture gives the critical surface energy $\gamma_{crit}$ as a measure of the surface energy γ of the particles. If the alcohol used is methanol, the methanol content in water gives the "methanol number".

In a preferred embodiment, the particles have a surface energy γ less than the surface tension γ of phase A, A1, A2, but greater than the surface tension γ of phase B, B1, B2. For particles according to the invention, which are preferably metal oxide particles, this means that the metal oxides are preferably partially hydrophobicized or partially silylated. According to the invention, partially silylated means that neither the entire metal oxide surface is unsilylated, nor that the entire metal oxide surface is silylated. The degree of coverage τ of the surface with silylating agent radicals is preferably 25%<τ<75%, based on the total metal oxide particle surface. Preferably, the contact angle $\theta_{particle}$ against phase A is 0°<$\theta_{particle}$<180°. Preferably, the contact angle $\theta_{particle}$ against water is 0°<$\theta_{particle}$<180°. The coverage with silylating agent may be ascertained by means of elemental analysis, such as the carbon content, or by determining the residual content of reactive surface OH groups of the metal oxide.

For pyrogenic silicon dioxide, partial silylation means that the content of nonsilylated surface silanol groups on the silicon dioxide surface fluctuates between at least 20% and at most 80% of the starting silicon dioxide; the starting silicon dioxide (100%) has 1.5-2.5 SiOH per $nm^2$ specific surface area, preferably 1.6-2.0. This means that the density of the surface silanol groups SiOH in the partially silylated silicon dioxide varies between a minimum of 0.3 and a maximum of 1.5 SiOH per $nm^2$ of particle surface. A silicon dioxide with a specific surface area of 200 $m^2$/g which is silylated, for example, will exhibit 0.1 mmol/g of SiOH to 0.5 mmol/g of SiOH, while a silicon dioxide with a lower or larger surface area, a linearly proportional greater or lesser content of surface silanol groups SiOH will be exhibited.

Complete water wetting of pyrogenic silicon dioxide arises when it has a carbon content of less than 0.1% by weight for a specific surface area of 100 $m^2$/g. For a silicon dioxide with a smaller or greater surface, this means a linearly proportional greater or lesser content of carbon will provide complete wetting. Preference is given to pyrogenic silicon dioxide which is not completely water-wettable, i.e. has a contact angle θ against water of preferably greater than 0°. Preference is also given to pyrogenic silicon dioxide which is not completely water-wettable, and has a carbon content of greater than 0.1% by weight for a specific surface area of 100 $m^2$/g. For a silicon dioxide with a smaller or greater surface, this means a linearly proportional greater or lesser content of carbon.

Preference is also given to pyrogenic silicon dioxide which exhibits incomplete water nonwettability and has a contact angle θ against water of preferably less than 180°. Preference is given to pyrogenic silicon dioxide which is not completely water-unwettable, and has a carbon content of less than 1% by weight for a specific surface area of 100 $m^2$/g. For a silicon dioxide with a smaller or greater surface, this means a linearly proportional greater or lesser content of carbon. Preferably, pyrogenic silicon dioxide which is not completely water-unwettable has a methanol number of less than 20 (see above).

Preference is given to using at least two types of particles with different surface properties; preferably, these particles with differing surface properties differ by virtue of the fact that at least one type of particles is not wetted by phase A, i.e. cannot be suspended in phase A. It is possible to use any desired mixtures of the abovementioned particles according to the invention. The novel properties of the particles can be achieved by one type of particle, but also by a suitable mixture of particles with differing properties.

The invention further provides a method of producing a (A1/B/A2) multiple emulsion, which comprises dispersing the particulate solids in the B phase and dispersing this dispersion or suspension in the A1 phase, and dispersing the emulsion formed in this way in the A2 phase which comprises the particulate solids. The term "dispersion" herein includes suspensions, when applicable.

The invention further provides a method of producing a (A1/B/A2) multiple emulsion, which comprises dispersing the particulate solids in the A1 phase and dispersing this dispersion or suspension in the B phase and dispersing the emulsion formed in this way in the A2 phase which comprises particulate solids.

Preparation of a Phase A1-in-phase B-in-phase A2 (A1/B/A2) or Water-in-oil-in-water (w/o/w) Multiple Emulsion Step (I)

Preparation of an A1/B Emulsion or w/o Emulsion.

To prepare the A1/B or w/o emulsion, it is possible to use all particles according to the invention. Preference is given to using particles which are not wetted by phase A, A1, A2. Preference is given to using particles which are wetted by phase B. Preference is given to using particles which are not wetted by water. Preference is given to using particles which are wetted by the oil phase.

If the particles used are metal oxides, then preference is given to those whose surface is at least 40% and at most 60% covered by hydrophobicizing agents, preferably silylating agents, i.e. the degree of coverage τ of hydrophobicizing agents, or silylating agents, is between 40% and 60%, and the content of uncovered surface is between at most 60% and 40% of the total surface.

If the particles used are pyrogenic silicas, then preference is given to those whose surface is at least 40% and at most 60% covered by hydrophobicizing agents, preferably silylating agents, i.e. the degree of coverage τ is between 40% and 60 %, and the content of nonsilylated surface silanol groups is between at most 60% and 40% of the silanol groups originally present. The total number of silanol groups is given by the sum of the residual silanol groups and the sum of the silylating agent radicals on the silica surface.

The particles can be dispersed in phase A1 or phase B. Preferably, the particles are dispersed in the phase in which they are wetted and thus dispersed more effectively.

The amount of particles according to the invention is greater than 0.1% by weight, preferably greater than 0.5% by weight, more preferably greater than 1% by weight, based on the weight phase A1 or phase B in which they are suitably dispersed. To prepare multiple emulsions which are stable against sedimentation an amount of particles according to the invention greater than 4% by weight is particularly preferred. The upper limit for the amount of particles is limited by rheology and viscosity of the particle-in-phase B or particle-in-oil or particle-in-phase A1 or particle-in-water suspension to be initially prepared. The upper limit of the amount of particles is arbitrary, with the proviso that a liquid, flowable and processable suspension is formed. The resulting viscosity is dependent on the particle size, the particle structure and the surface properties of the particles.

For theological reasons, for example, the maximum concentration of silylated pyrogenic silica with a BET specific surface area of 250 $m^2/g$ during the preparation of a suspension in oil phase is less than 25% by weight, preferably less than 10% by weight, and more preferably less than 5% by weight in the oil phase, but the maximum concentration of silylated pyrogenic silica with a BET specific surface area of 40 $m^2/g$ during the preparation of a suspension in oil phase is less than 75% by weight, preferably less than 40% by weight, more preferably less than 15% by weight.

In order to make technical handling easier, the phase B or oil phase is initially introduced, and particles are added. The mixture is then dispersed by means of suitable methods, particular preference being given to methods which achieve complete or virtually complete dispersion of the particles, flocs, clusters or agglomerates, such as ultrasound homogenizers, ultrasound tips or transmitters with frequencies of from 1 to 100 kHz, typically 20 kHz, with energy outputs of from 10 to 1000 $W/cm^2$, typically 100 to 500 $W/cm^2$, such as sonolators, high-speed rotor-stator units with rotary speeds of from 5,000 to 20,000 rotations per minute, preferably 10,000-15,000 rotations per minute. Dispersion is carried out over 1 to 60 min, preferably for 1.5 to 5 min.

0.1 to 0.5 part by weight, preferably 0.15 to 0.25 part by weight, of phase A1 or water phase are added to the suspension particle-in-phase B, giving a total amount of 1.0 part by weight, and emulsified using methods suitable for the preparation of emulsions. Typically, equipment suitable for this purpose includes high-speed rotor-stator units with rotary speeds of from 5,000 to 20,000 rotations per minute, preferably 10,000-15,000 rotations per minute. Emulsification is carried out over 1 to 60 min, preferably for 1.5 to 5 min.

Step (II)

Preparation of (A1/B/A2) or (w/o/w) Multiple Emulsion

To prepare the A1/B/A2 or w/o/w multiple emulsion it is possible to use all the particles according to the invention. Preference is given to using particles which are wetted by phase A, A2. Preference is given to using particles which are wetted by phase B. Preference is given to using particles which are wetted by water. preference is given to using particles which are wetted by the oil phase.

If the particles used are metal oxides, then preference is given to those whose surface is at least 20% and at most 40% covered by hydrophobicizing agents, preferably silylating agents, i.e. the degree of coverage τ of hydrophobicizing agents, or silylating agents, is between 20% and 40%, and the content of uncovered surface is between at most 80% and at least 60% of the total surface.

If the particles used are pyrogenic silicas, then preference is given to those whose surface is at least 20% and at most 40% covered by hydrophobicizing agents, preferably silylating agents, i.e. the degree of coverage τ is between 20% and 40%, and the content of nonsilylated surface silanol groups is between at most 80% and at least 60% of the silanol groups originally present. The total number of silanol groups is given by the sum of the remaining silanol groups and the sum of the silylating agent radicals on the silica surface.

The amount of particles according to the invention is greater than 1% by weight, preferably greater than 3% by weight, more preferably greater than 4% by weight, based on the weight of phase A2.

The upper limit for the amount of particles is restricted by rheology and viscosity of the particle-in-phase A2 or particle-in-water suspension to be prepared initially. The upper limit of the amount of particles in phase A, A2 is arbitrary with the proviso that a liquid, flowable and processable suspension is formed. The resulting viscosity is dependent on the particle size, the particle structure and the surface properties of the particles.

For rheological reasons, for example, the maximum concentration of pyrogenic silica with a BET specific surface area of 275 $m^2/g$ during the preparation of an aqueous suspension is less than 15% by weight, preferably less than 10% by weight, more preferably less than 5% by weight in the water phase, but the maximum concentration of pyrogenic silica with a BET specific surface area of 45 $m^2/g$ during the preparation of an aqueous suspension is less than 50% by weight, preferably 25% by weight, more preferably less than 10% by weight.

By means of the amount, in % by weight, of particles based on phase A2, it is possible to control the average diameter of the external emulsion droplets w/o/w in a targeted manner, typically to be in the range 1 μm to 500 μm, for a stable multiple emulsion preferably less than 100 μm, more preferably less than 30 μm; the larger the amount of particles, the smaller the average diameter of the emulsion droplets.

In order to make technical handling easier, the phase A2 or aqueous phase is initially introduced, and particles are added. The mixture is then dispersed by means of suitable methods, particular preference being given to methods which achieve complete or virtually complete dispersion of the particles, flocs, clusters or agglomerates, such as ultrasound homogenizers, ultrasound tips or transmitters with frequencies of form 1 to 100 kHz, typically 20 kHz, outputs of from 10 to 1000 $W/cm^2$, typically 100 to 500 $W/cm^2$, such as sonolators, high-speed rotor-stator units with rotary speeds of from 5,000 to 20,000 rotations per minute, preferably 10,000-15,000 rotations per minute. Dispersion is carried out over 1 to 60 min, preferably for 1.5 to 5 min.

0.1 to 0.5 part, preferably 0.15 to 0.25 part of emulsion phase A1-in-phase B (A1/B), or water-in-oil (w/o) are added to the suspension particles-in-phase A2, so that a total amount of 1.0 part by weight results, and gently emulsified using processes suitable for the preparation of emulsions. By "gentle" is meant that the shear energy introduced into the system is less than 10%, preferably less than 5%, more preferably less than 1%, of the energy introduced in the preparation of the A1/B or w/o emulsion, high-speed rotor stator units having rotational speeds of from 5,000 to 15,000 revolutions per minute, preferably 8,000 to 13,000, more preferably 13,000 revolutions per minute typically being suitable for this purpose. Emulsification takes place over the course of 1 to 120 seconds, preferably 5 to 25 seconds.

The invention further provides a method of producing a (B1/A/B2) multiple emulsion, which comprises dispersing the particulate solids in the B1 phase, and dispersing this suspension in the A phase, and dispersing the emulsion formed in this way in the B2 phase which comprises particulate solids.

The invention further provides a method of producing a (B1/A/B2) multiple emulsion, which comprises dispersing the particulate solids in the A phase and dispersing this suspension in the B1 phase, and dispersing the emulsion formed in this way in the B2 phase which comprises particulate solids.

Preparation of a Phase B1-in-phase A-in-phase B2 (B1/A/B2) or Oil-in-water-in-oil (o/w/o) Multiple Emulsion Step (I)

Preparation of B1/A Emulsion or o/w Emulsion

The particles can be dispersed in phase A or phase B1 . Preferably, the particles are dispersed in the phase in which they are wetted and are thus dispersed more effectively.

The amount of particles according to the invention is greater than 1% by weight, preferably greater than 2% by weight, more preferably greater than 4% by weight, based on the weight of phase B1 or phase A in which they are suitably dispersed.

The upper limit for the amount of particles is restricted by rheology and viscosity of the particles-in-phase A or particles-in-water or particles-in-phase B1 suspension to be prepared initially. The upper limit of the amount of particles here is arbitrary, with the proviso that a liquid, flowable and processable suspension is formed. The resulting viscosity is dependent on the particle size, the particle structure and the surface properties of the particles.

For rheological reasons, for example, the maximum concentration of pyrogenic silica with a BET specific surface area of 275 $m^2/g$ during the preparation of an aqueous suspension is less than 15% by weight, preferably less than 10% by weight, more preferably less than 5% by weight in the water phase, but the maximum concentration of pyrogenic silica with a BET specific surface area of 45 $m^2/g$ during the preparation of aqueous suspension is less than 50% by weight, preferably less than 25% by weight, more preferably less than 10% by weight.

To prepare the B1/A or o/w emulsion, it is possible to use all particles according to the invention. Preference is given to using particles which are wetted by phase A. Preference is given to using particles which are wetted by phase B. Preference is given to using particles which are wetted by water. Preference is given to using particles which are wetted by the oil phase.

If the particles used are metal oxides, then preference is given to those whose surface is at least 20% and at most 40% covered by hydrophobicizing agents, preferably silylating agents, i.e. the degree of coverage $\tau$ of hydrophobicizing agents, or silylating agents, is between 20% and 40%, and the content of uncovered surface is between at most 80% and at least 60% of the total surface.

If the particles used are pyrogenic silicas, then preference is given to those whose surface is at least 20% and at most 40% covered by hydrophobicizing agents, preferably silylating agents, i.e. the degree of coverage $\tau$ is between 20% and 40%, and the content of nonsilylated surface silanol groups is between at most 80% and 60% of the silanol groups originally present. The total number of silanol groups is given by the sum of the remaining silanol groups in the sum of the silylating agent radicals on the silica surface.

In order to make technical handling easier, the phase A or aqueous phase is initially introduced, and particles are added. The mixture is then dispersed by means of suitable methods, particular preference being given to methods which achieve complete or virtually complete dispersion of the particles, flocs, clusters or agglomerates, such as ultrasound homogenizers, ultrasound tips or transmitters with frequencies of form 1 to 100 kHz, typically 20 kHz, and energy outputs of from 10 to 1000 $W/cm^2$, typically 100 to 500 $W/cm^2$, such as sonolators, high-speed rotor-stator units with rotary speeds of from 5,000 to 20,000 rotations per minute, preferably 10,000-15,000 rotations per minute. Dispersion is carried out over 1 to 60 min, preferably for 1.5 to 5 min.

0.1 to 0.5 part, preferably 0.15 to 0.25 part, of phase B1 or oil phase are added to the suspension particles-in-phase A and emulsified using processes suitable for the preparation of emulsions. Typically suitable are high-speed rotor-stator units with rotary speeds of from 5,000 to 20,000 revolutions per minute, preferably 10,000-15,000 revolutions per minute. Emulsification is carried out over the course of 1 to 60 min, preferably 1.5 to 5 min.

Step (II)

Preparation of a (B1/A/B2) or (o/w/o) Multiple Emulsion

To prepare the B1/A/B2 or o/w/o multiple emulsion, it is possible to use all particles according to the invention. Preference is given to using particles which are not wetted by phase A. Preference is given to using particles which are wetted by phase B. Preference is given to using particles which are not wetted by water. Preference is given to using particles which are wetted by the oil phase.

If the particles used are metal oxides, then preference is given to those whose surface is at least 40% and at most 60% covered by hydrophobicizing agents, preferably silylating agents, i.e. the degree of coverage $\tau$ of hydrophobicizing agents, or silylating agents, is between 40% and 60%, and the content of uncovered surface is between at most 60% and at least 40% of the total surface.

If the particles used are pyrogenic silicas, then preference is given to those whose surface is at least 40% and at most 60% covered by hydrophobicizing agents, preferably silylating agents, i.e. the degree of coverage $\tau$ is between 40% and 60%, and the content of nonsilylated surface silanol groups is between at most 60% and at least 40% of the silanol groups originally present. The total number of silanol groups is given by the sum of the remaining silanol groups and the sum of the silylating agent radicals on the silica surface.

The amount of particles according to the invention is greater than 0.1% by weight, preferably greater than 0.5% by weight, more preferably greater than 1% by weight, based on the weight of phase B2. To prepare multiple emulsions stable against sedimentation, an amount of more than 4% by weight of particles according to the invention is particularly preferred.

The upper limit for the amount of particles is restricted by rheology and viscosity of the particles-in-phase B2 or particles-in-oil suspension to be prepared initially. The upper limit of the amount of particles in phase B2 is arbitrary with the proviso that a liquid, flowable and processable suspension is formed. The resulting viscosity is dependent on the particle size, the particle structure and the surface properties of the particles.

For rheological reasons, for example, the maximum concentration of silylated pyrogenic silica with a BET specific surface area of 250 $m^2/g$ during the preparation of a suspension in the oil phase is less than 30% by weight, preferably less than 15% by weight, more preferably less than 5% by weight in the water phase, but the maximum concentration of silylated pyrogenic silica with a BET specific surface area of 40 $m^2/g$ during the preparation of the suspension in the oil phase is less than 75% by weight, preferably less than 50% by weight, more preferably less than 25% by weight.

By means of the amount, in % by weight, of particles based on phase B2, it is possible to control the average diameter of the external emulsion droplets o/w/o in a targeted manner, typically to be in the range 1 μm to 500 μm, for a stable emulsion less than 100 μm, preferably less than 30 μm. The greater the amount of particles, the smaller the average diameter of the emulsion droplets.

In order to make industrial handling easier, the phase B2 or oil phase is initially introduced, and particles are added. The mixture is then dispersed by means of suitable methods, particular preference being given to methods which achieve complete or virtually complete dispersion of the particles, flocs, clusters or agglomerates, such as ultrasound homogenizers, ultrasound tips or transmitters with frequencies of from 1 to 100 kHz, typically 20 kHz, and energy outputs of from 10 to 1000 $W/cm^2$, typically 100 to 500 $W/cm^2$, such as sonolators, high-speed rotor-stator units with rotary speeds of from 5,000 to 20,000 rotations per minute, preferably 10,000-15,000 rotations per minute. Dispersion is carried out over 1 to 60 min, preferably for 1.5 to 5 min.

Oil-in-water (o/w) in the Oil Phase 0.1 to 0.5 part, preferably 0.15 to 0.25 part of emulsion phase B1 -in-phase A (B1/A) or oil-in-water (o/w) are added to the suspension particles-in-phase B2, so that a total amount of 1.0 part by weight results, and gently emulsified using methods suitable for the preparation of emulsions. "Gentle" means that the shear energy introduced into the system is less than 10%, preferably less than 5%, more preferably less than 1% of the energy of the preparation of the B1/A or o/w emulsion, high-speed rotor-stator units with rotary speeds of from 5,000 to 15,000 revolutions per minute, preferably 8,000 to 13,000, more preferably 13,000 revolutions per minute, being suitable for this purpose. Emulsification is carried out over the course of 1 to 120 seconds, preferably 5 to 25 seconds.

Phases A, A1, A2 can contain dissolved solids. Examples are soluble inorganic or organic compounds which have no or only very slight surface-active properties and do not change the conductivity and the pH of phases A, A1, A2 and B, B1, B2 beyond the permissible limits given below.

If A is water, which is preferable, examples of inorganic compounds which are soluble in water include mineral salts such as sodium chloride, calcium chloride, sodium sulfate, copper nitrate, copper sulfate, potassium cyanide etc. or mineral acids, such as hydrochloric acid. Examples of organic compounds which are soluble in water are sugars, saccharides, polysaccharides, glycerols, organic acids such as formic acid, citric acid, or salts thereof such as formates, e.g. sodium formate, or acetates such as copper acetate, or water-soluble polymers such as gum arabic (gua gum), cellulose, etc.

Phase B, B1, B2 can contain dissolved solids. Examples of soluble inorganic or organic compounds, polymers, waxes, resins which do not have surface-active properties and do not change the conductivity and the pH of phase A or B beyond the permissible limits given below are suitable, e.g. liquid solutions of paraffin waxes in a lower alkane, e.g. decane.

Additional insoluble particles of all types are permissible.

Surface-active substances (surfactants) are permissible up to a maximum concentration which is less than 0.1 times the critical micelle concentration (in phase A, A1, A2 or in water) (cmc=critical micelle concentration), preferably less than 0.01 times the cmc.

The pH can be varied without limitations, with the proviso that the phases A, A1, A2 and/or B, B1, B2 do not change chemically and that the particles are not dissolved or disintegrated. If particles are preferably pyrogenic silica, for example, this means that $2<pH<10$ for an aqueous system.

The ionic strength of the two phases, A, A1, A2 and B, B1, B2, in particular phases A, A1, A2, per liter, is preferably less than 1 mol, preferably less than 0.1 mol, more preferably less than 0.01 mol, and most preferably less than 0.001 mol. For example, when employing the salt sodium chloride, NaCl, less than 1 mol, preferably less than 0.1 mol, more preferably less than 0.01 mol, and most preferably less than 0.001 mol of this salt is present per liter.

Applications

The invention further provides for the use of the multiple emulsion in pharmaceuticals, cosmetics, medicinal products, foodstuffs, animal feeds, agrochemical compositions, and catalysts. The invention further provides for the use of the multiple emulsion for the controlled and controlled delayed release of active ingredients to the surrounding area.

Multiple emulsions can be used in controlled release application in which an active ingredient of an A1-in-B-in-A2 or B1 -in-A-in-B2 multiple emulsion dissolved in phase A1 or phase B1 is released to the surrounding area in a slow and controlled manner. Application fields include those of pharmacy, medicine, agrochemistry, foods, animal nutrition, cosmetics, in chemical catalysis, and surface coatings, in particular for paper, metals, plastics, stone, and building materials.

EXAMPLES

Example 1

According to the Invention of a w/o/w Multiple Emulsion

Step 1

1 g of a hydrophobic pyrogenic silica silylated with dimethylsiloxy groups (obtainable under the name Wacker HDK H30 from Wacker-Chemie GmbH, prepared by silylation of a pyrogenic silica with a BET surface area of 300 $m^2$/g) with a carbon content 1.8% by weight and a content of surface silanol groups of 0.83 mmol/g (corresponding to a residual content of surface silanol groups of 51% relative to the starting silica) is added to 80 ml of a triglyceride of average chain length, as is typically used in foodstuffs and animal feeds, number 810N, and then the mixture is dispersed using an ultrasound transmitter (Sonics & Material, 20 kHz at 10 W for 2 minutes). 20 ml of demineralized water are then added and the mixture is emulsified using an Ultra-Turrax rotor-stator homogenizer (1.8 cm diameter) at 13,000 rpm for 2 minutes. This gives a stable w/o emulsion.

Droplet sizes with light diffraction (Malvern MasterSizer MS20)

1 g HDK H30 13 µm (this is as per the abovementioned Example 1)

2 g HDK H30 8 µm (with change to the abovementioned Example 1)

3 g HDK H30 5 µm (with change of the abovementioned Example 1)

Step 2

1 g of a pyrogenic silica silylated with dimethylsiloxy groups (obtainable under the name Wacker HDK H30ED from Wacker-Chemie GmbH, prepared by silylation of a pyrogenic silica with a BET surface area of 300 $m^2$/g) with a carbon content of 0.8% by weight and a content of surface silanol groups of 0.68 mmol/g (corresponding to a residual content of surface silanol groups of 79% relative to the starting silica) is added to 80 ml of (demineralized) water, and then the mixture is dispersed using an ultrasound transmitter (Sonics & Material, 20 kHz at 10 W for 2 minutes). 20 ml of the above-described w/o emulsion are then added and the mixture is emulsified with an Ultra-Turrax rotor-stator homogenizer (1.8 cm diameter) at 11,000 rpm for 10 seconds. This gives a w/o/w multiple emulsion which is stable for more than 15 months, is stable against shearing, and which does not exhibit coalescence of any kind.

FIG. 1*a* is a photomicrograph of the w/o/w multiple emulsion. The scale is 50 micrometers.

Figure 1B:
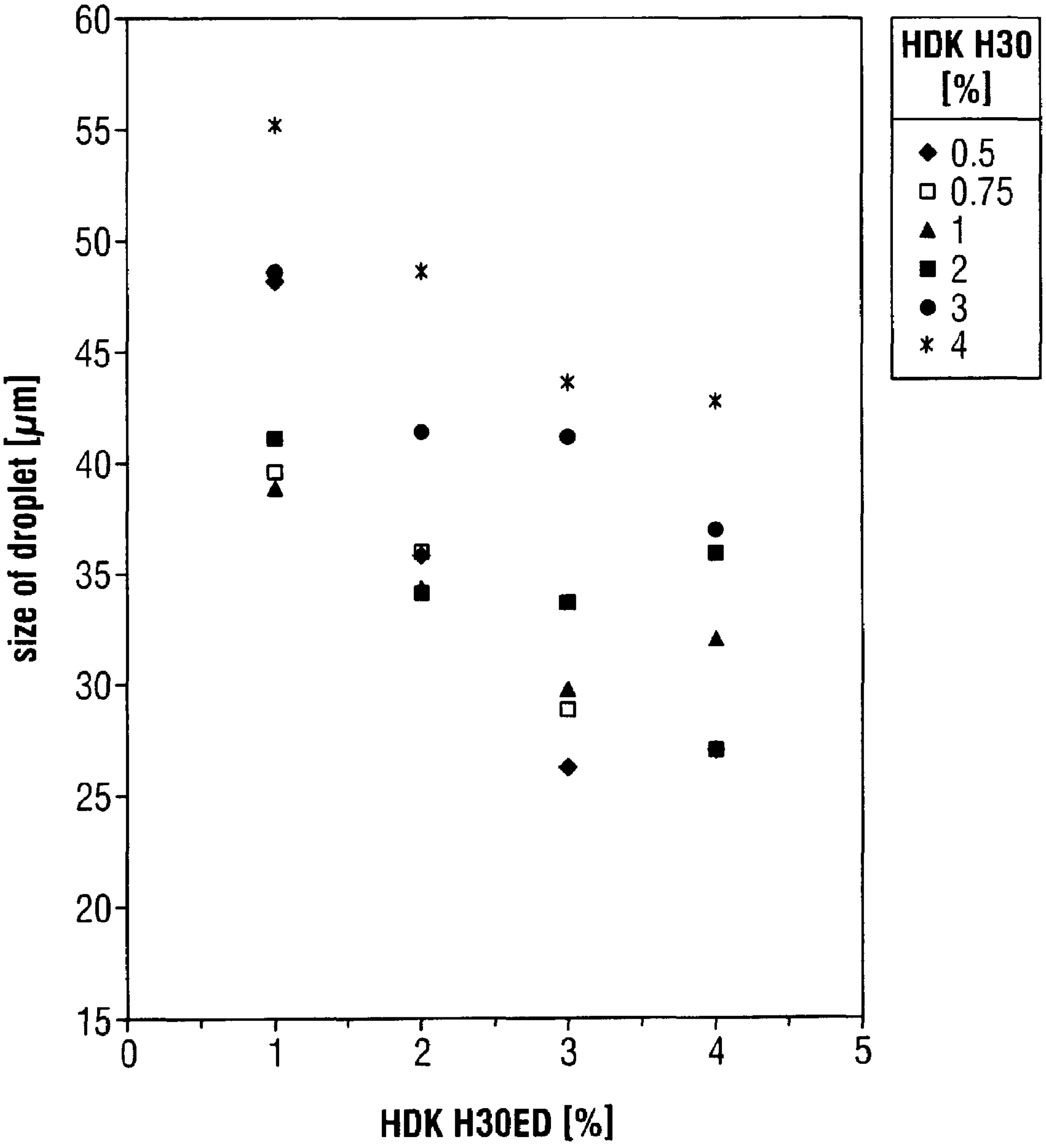
FIG. 1*b* plots droplet sizes in μm (ordinate) versus particle concentration (abscissa) in the continuous water phase at different particle concentrations in the oil phase (legend) of one embodiment of the subject invention.

Droplet sizes in micrometers (µm) are measured by light diffraction (Malvern Master Sizer MS20). The size of the external (w/o) droplets in (w) as a function of the concentration of silica HDK H30 (see legend in FIG. 1*b*: HDK H30=0.5%; 0.75%; 1%; 2%; 3%, 4%) and as a function of the concentration of the silica HDK H30ED (see abscissa: 1%; 2%, 3%,4%) in Example 1.

Example 2

According to the Invention of a w/o/w Multiple Emulsion

Step 1

1 g of a hydrophobic pyrogenic silica silylated with dimethylsiloxy groups (obtainable under the name HDK H30 from Wacker-Chemie GmbH, prepared by silylation of a pyrogenic silica with a BET surface area of 300 $m^2$/g) with a carbon content of 1.8% by weight and a content of surface silanol groups of 0.83 mmol/g (corresponding to a residual content of surface silanol groups of 51%, relative to the starting silica) is added to 80 ml of toluene, and then the mixture is dispersed using an ultrasound transmitter (Sonics & Material, 20 kHz at 10 W for 2 minutes). 20 ml of demineralized water are then added and the mixture is emulsified using an Ultra-Turrax rotor-stator homogenizer (1.8 cm diameter) at 13,000 rpm for 2 minutes. This gives a stable w/o emulsion.

Step 2

1 g of a pyrogenic silica silylated with dimethylsiloxy groups (obtainable under the name Wacker HDK H30ED from Wacker-Chemie GmbH, prepared by silylation of a pyrogenic silica with a BET surface area of 300 $m^2$/g) with a carbon content of 0.8% by weight and a content of surface silanol groups of 0.68 mmol/g (corresponding to a residual content of surface silanol groups of 79%, relative to the starting silica) is added to 80 ml of demineralized water, and then the mixture is dispersed with an ultrasound transmitter (Sonics & Material, 20 kHz at 10 W for 20 minutes). 20 ml of the above-described w/o emulsion are then added and the mixture is emulsified with an Ultra-Turrax rotor-stator homogenizer (1.8 cm diameter) at 11,000 rpm for 10 seconds. This gives a w/o/w multiple emulsion which is stable for more than 15 months, stable against shearing, and which does not exhibit coalescence of any kind.

particle sizes measured by light diffraction (Malvern MasterSizer MS20) showed internal (w) droplets in (o) of 0.8 µm average size, in external (w/o) droplets in (w) of 26 µm.

Figure 2:
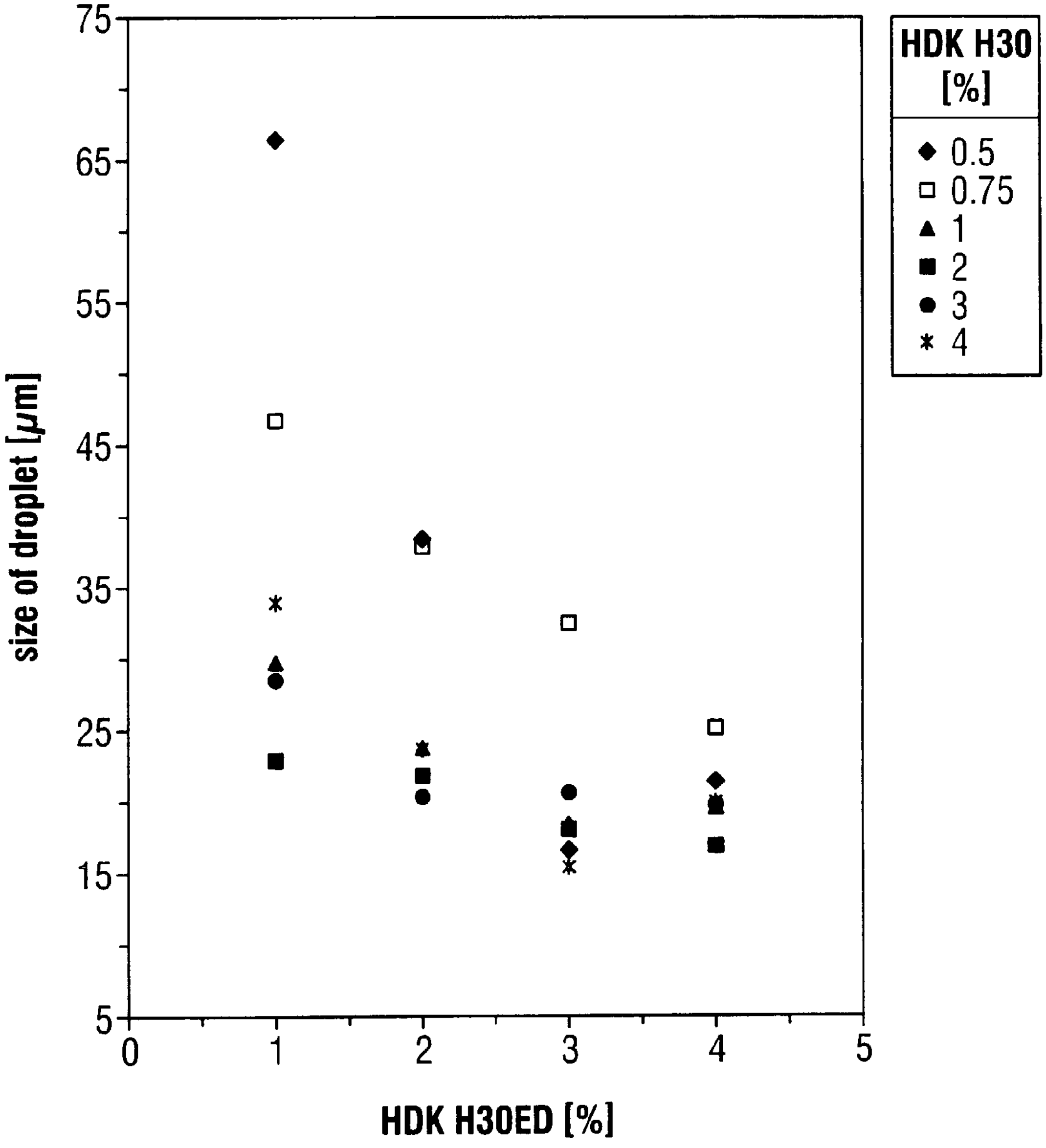
FIG. 2 plots droplet sizes in μm (ordinate) versus particle concentration (abscissa) in the continuous water phase at different particle concentrations in the oil phase (legend) of a further embodiment of the subject invention.

Droplet sizes in micrometers (µm) measured by light diffraction (Malvern MasterSizer MS20) at various particle concentrations are presented in FIG. 2. The size of the external (w/o) droplets in (w) as a function of the concentration of silica HDK H30 (see legend in FIG. 2: HDK H30=0.5%; 0.75%; 1%; 2%; 3%, 4%) and as a function of the concentration of the silica HDK H30ED (see abscissas: 1%; 2%, 3%, 4%) in Example 2 are shown.

Example 3

An o/w/o Multiple Emulsion

Step 1

3 g of a hydrophobic pyrogenic silica silylated with dimethylsiloxy groups (obtainable under the name Wacker HDK H20ED from Wacker-Chemie GmbH, prepared by silylation of a pyrogenic silica with a BET surface area of 200 $m^2$/g) with a carbon content of 0.6% by weight and a content of surface silanol groups of 0.44 mmol/g (corresponding to a residual content of surface silanol groups of 80%, relative to the starting silica) are added to 80 ml of demineralized water, and then the mixture is dispersed using an ultrasound transmitter (Sonics & Material, 20 kHz at 10 W for 2 minutes). Then, 20 ml of toluene are added and the mixture is emulsified using an Ultra-Turrax rotor-stator homogenizer (1.8 cm diameter) at 13,000 rpm for 2 minutes. This gives a stable o/w emulsion.

Step 2

Figure 3:
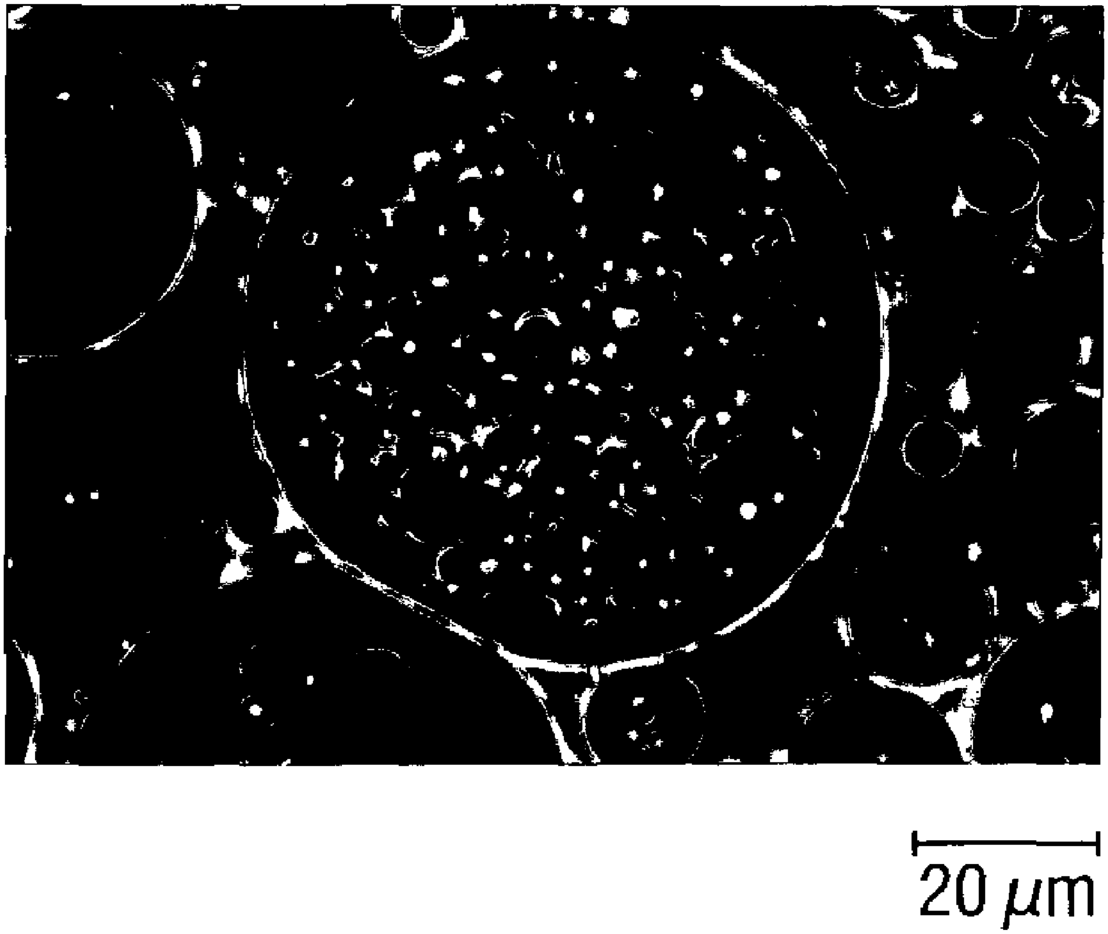
FIG. 3 is a photomicrograph of an oil/water/oil multiple emulsion of the present invention.

3 g of a pyrogenic silica silylated with dimethylsiloxy groups (obtainable under the name Wacker HDK H20 from Wacker-Chemie GmbH, prepared by silylation of a pyrogenic silica with a BET surface area of 200 $m^2/g$) with a carbon content of 1.1% by weight and a content of surface silanol groups of 0.31 mmol/g (corresponding to a residual content of surface silanol groups of 51%, relative to the starting silica) are added to 80 ml of toluene and then the mixture is dispersed using an ultrasound transmitter (Sonics & Material, 20 kHz at 10 W for 2 minutes). Then, 20 ml of the above-described o/w emulsion are added and the mixture is emulsified with an Ultra-Turrax rotor-stator homogenizer (1.8 cm diameter) at 11,000 rpm for 10 seconds. This gives an oil-in-water-in-oil (o/w/o) multiple emulsion which is stable for over 15 months, stable against shearing, and which does not exhibit coalescence of any kind. A photomicrograph of the w/o/w multiple emulsion is presented as FIG. 3: scale, 20 micrometers.

Example 4

Controlled Release Function of the w/o/w Multiple Emulsion from Example 2

The procedure is as described in Example 2 except that sodium chloride is additionally added to the internal first water phase from step 1 in a total concentration of 4a) 0.01 mol/l, 4b) 0.02 mol/l, 4c) 0.05 mol/l, 4d) 0.1 mol/l, 4e) 0.2 mol/l and 4f) 0.5 mol/l, and in step 2 glucose is added to the external third phase, likewise a water phase, in an amount such that an isotonic equilibrium between the internal water phase (step 1) and external water phase (step 2) prevails (to balance the osmotic pressure). This is a typical procedure in order to achieve real controlled release conditions and not to destroy the multiple emulsion under a prevailing osmotic pressure.

Figure 4:
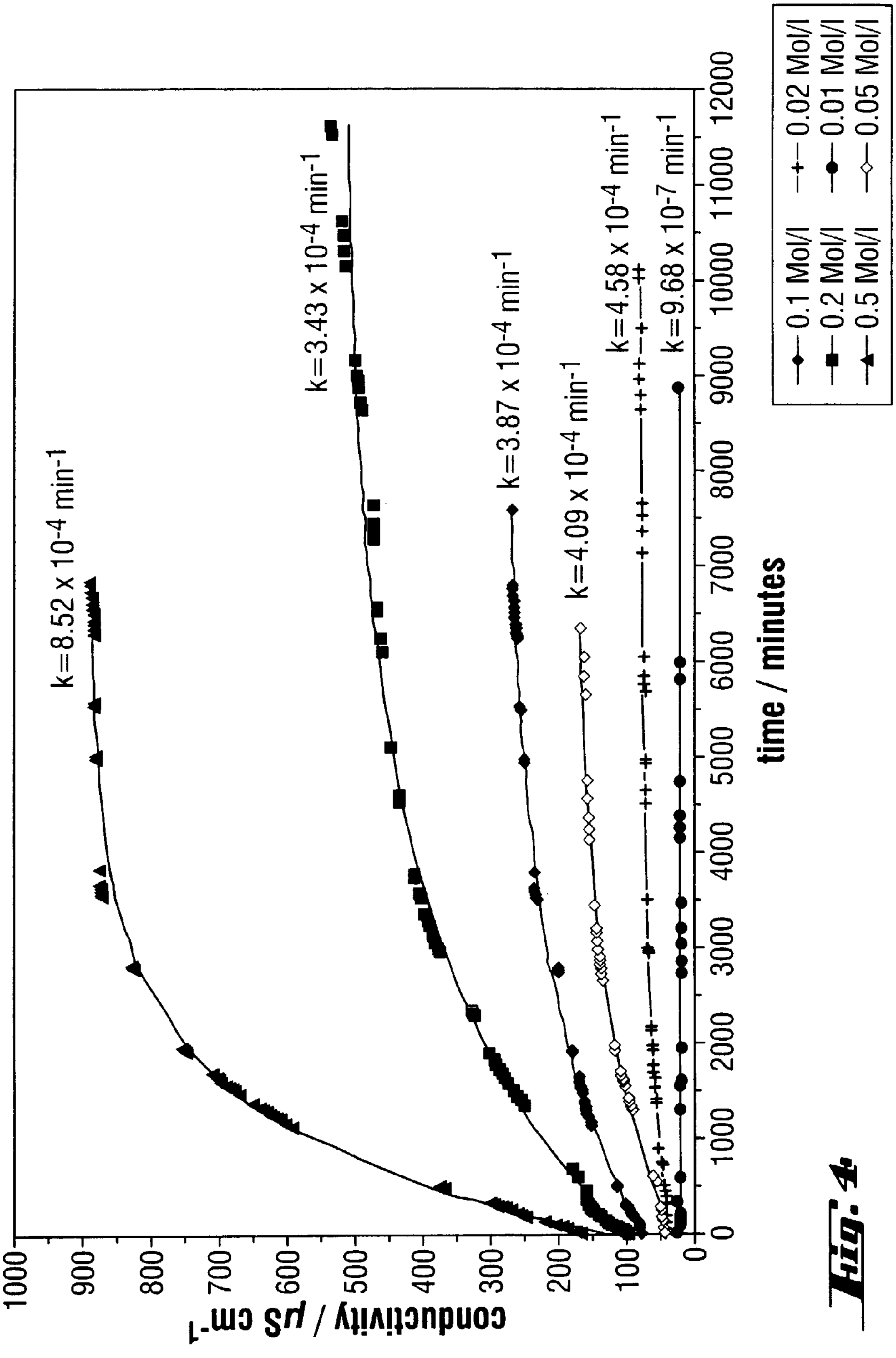
FIG. 4 illustrates one use of the subject invention multiple emulsions as timed release compositions for active substances.

The change, with time, of the conductivity in the external water phase w/o/w, as a measure of the transition of sodium chloride from the internal w/o/w to the external w/o/w water phase, is measured. The typical increase with time based on a controlled release process is obtained, see FIG. 4.

Comparative Example C5

Noninventive Reference Example in which a Surface-active Substance is Additionally Used Step 1

1 g of a hydrophobic pyrogenic silica silylated with dimethylsiloxy groups (obtainable under the name Wacker HDK H30 from Wacker-Chemie GmbH, prepared by silylation of a pyrogenic silica with a BET surface area of 300 $m^2/g$) with a carbon content of 1.8% by weight and a content of surface silanol groups of 0.83 mmol/g (corresponding to a residual content of surface silanol groups of 51%, relative to the starting silica) is added to 80 ml of toluene, and then the mixture is dispersed using an ultrasound transmitter (Sonics & Material, 20 kHz at 10 W for 2 minutes). 20 ml of demineralized water are then added and the mixture is emulsified using an Ultra-Turrax rotor-stator homogenizer (1.8 cm diameter) at 13,000 rpm for 2 minutes. This gives a stable w/o emulsion.

Step 2

1 g of a pyrogenic silica silylated with dimethylsiloxy groups (obtainable under the name Wacker HDK H30ED from Wacker-Chemie GmbH, prepared by silylation of a pyrogenic silica with a BET surface area of 300 $m^2/g$) with a carbon content of 0.8% by weight and a content of surface silanol groups of 0.68 mmol/g (corresponding to a residual content of surface silanol groups of 79%, relative to the starting silica) is added to 80 ml of demineralized water, and then the mixture is dispersed using an ultrasound transmitter (Sonics & Material, 20 kHz at 10 W for 2 minutes). 20 ml of the above-described w/o emulsion are then added and the mixture is emulsified using an Ultra-Turrax rotor-stator homogenizer (1.8 cm diameter) at 11,000 rpm for 10 seconds. This gives a w/o/w multiple emulsion which is stable for over 15 months, stable against shearing, and which does not exhibit coalescence of any kind.

Step 3

15 months after step 2, 0.1 ml of a 0.1 molar solution of the surface-active substance SDS (sodium dodecyl sulfate) in water is added to 10 ml of the stable w/o/w multiple emulsion from step 2. The mixture is shaken, at room temperature of T=20° C. The w/o/w multiple emulsion breaks and a solid sediment forms.

Example 6

According to the Invention of a w/o/w Multiple Emulsion

Step 1

5 g of a hydrophobic pyrogenic silica silylated with dimethylsiloxy groups (obtainable under the name Wacker HDK H30 from Wacker-Chemie GmbH, prepared by silylation of the pyrogenic silica with a BET surface area of 300 $m^2/g$) with a carbon content of 1.8% by weight and a content of surface silanol groups of 0.83 mmol/g (corresponding to a residual content of surface silanol groups of 51%, relative to the starting silica) are added to 80 ml of toluene, and then the mixture is dispersed using an ultrasound transmitter (Sonics & Material, 20 kHz at 10 W for 2 minutes). 20 ml of demineralized water are then added, and the mixture is emulsified using an Ultra-Turrax rotor-stator homogenizer (1.8 cm diameter) at 13,000 rpm for 2 minutes. This gives a stable w/o emulsion.

Step 2

5 g of a pyrogenic silica silylated with dimethylsiloxy groups (obtainable under the name Wacker HDK H30ED from Wacker-Chemie GmbH, prepared by silylation of a pyrogenic silica with a BET surface area of 300 $m^2/g$) with a carbon content of 0.8% by weight and a content of surface silanol groups of 0.68 mmol/g (corresponding to a residual content of surface silanol groups of 79%, relative to the starting silica) are added to 80 ml of demineralized water, and then the mixture is dispersed using an ultrasound transmitter (Sonics & Material, 20 kHz at 10 W for 2 minutes). 20 ml of the above-described w/o emulsion are then added and the mixture is emulsified using an Ultra-Turrax rotor-stator homogenizer (1.8 cm diameter) at 11,000 rpm for 10 seconds. This gives a viscous w/o/w multiple emulsion which is stable for over 15 months, stable against shearing, and which does not exhibit either coalescence or sedimentation of any kind.

Comparative Example C7

Noninventive Reference Example in which Only a Surface-active Substance is Used

The procedure is as in example 2 according to the invention, except that instead of the pyrogenic silica, 1 g of sodium dodecyl sulfate is used.

In step 1, a stable w/o emulsion is formed. However, in step 2, a multiple emulsion is formed which immediately breaks and coalesces.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A multiple emulsion which is stable against coalescence, comprising a composition A1/B/A2 or B1/A/B2, wherein A, A1, and A2 are polar phases and B, B1, and B2 are non-polar phases, and at least first and second particulate silica dispersants, each having mean particle sizes less than 1 μm, the first silica dispersant wettable by a phase A, A1, or A2 contained in the multiple emulsion and also wettable by a phase B, B1, or B2 contained in the multiple emulsion, the second silica dispersant wettable by a phase B, B1, or B2 contained in the multiple emulsion, but not wettable by a phase A, A1, or A2 contained in the multiple emulsion, said multiple emulsions prepared by a process comprising:

a) when the multiple emulsion is an A1/B/A2 multiple emulsion, preparing an A1/B emulsion by emulsifying A1 into B in the presence of said second silica dispersant, dispersing said first silica dispersant in A2, and dispersing the A1/B emulsion into A2, forming an A1/B/A2 multiple emulsion, or b) when the multiple emulsion is a B1/A/B2 multiple emulsion, preparing a B1/A emulsion by emulsifying B1 into A in the presence of said first silica dispersant, dispersing said second silica dispersant into the B2 phase, and dispersing the B1/A emulsion into B2, forming a B1/A/B2 multiple emulsion, wherein the multiple emulsion contains less than or equal to 0.1 times the critical micelle concentration of surface active substances in the polar phases A, A1, and A2, such that in the absence of said silica dispersants, a multiple emulsion containing less than or equal to 0.1 times the critical micelle concentration of surface active substances exhibits coalescence.

2. The multiple emulsion of claim 1, wherein said first silica dispersant has a contact angle θ in air with a polar phase A, A1, or A2 of $0<\theta<180°$.

3. The multiple emulsion of claim 1, wherein said first silica dispersant has a contact angle θ in air with a polar phase A, A1, or A2 of $60°\leqq\theta\leqq120°$.

4. The multiple emulsion of claim 1, wherein said first silica dispersant has a contact angle θ in air with water of $60°\leqq\theta\leqq120°$.

5. The multiple emulsion of claim 1, wherein the first silica dispersant is only partly wettable by water, and completely wettable by a nonpolar phase B, B1, or B2.

6. The multiple emulsion of claim 1, wherein the first silica dispersant is a pyrogenic silica having a mean particle size of less than 300 nm, is partly silylated, and has a residual density of surface silanol groups of 0.3 to 1.5 Si—OH per $(nm)^2$ of surface area.

7. The multiple emulsion of claim 1, wherein each of polar phases A, A1, and A2, when present, is an aqueous phase.

8. The A1/B/A2 multiple emulsion of claim 1, wherein in step a) the second silica dispersant is first dispersed in B, and then A1 is emulsified into B.

9. The B1/A/B2 multiple emulsion of claim 1, wherein in step b) the first silica dispersant is first dispersed in A, and then B1 is emulsified into A.

10. The multiple emulsion of claim 1, wherein said first and said second silica dispersants are silylated pyrogenic silica dispersants, the second silica dispersant having a lesser residual concentration of surface Si—OH groups than said first silica dispersant.

11. The multiple emulsion of claim 1, wherein said first silica dispersant and said second silica dispersant are present in the multiple emulsion in a weight ratio of 1:4 to 4:1.

12. The multiple emulsion of claim 1, which is free of surface active substances.

13. The multiple emulsion of claim 1, wherein a non-polar phase B, B1, or B2 additionally contains a first silica dispersant in addition to said second silica dispersant.

14. The multiple emulsion of claim 1 wherein at least one dispersed phase contains a pharmaceutical agent for which timed release is desired.

* * * * *